United States Patent [19]

Leeming et al.

[11] 4,011,343
[45] Mar. 8, 1977

[54] TRIAZAPENTADIENES AS ACARICIDES AND INSECTICIDES

[75] Inventors: Michael Raymond Graves Leeming, Canterbury; Alexander Ballingall Penrose, Eastry near Sandwich, both of England

[73] Assignee: Pfizer Inc., New York, N.Y.

[22] Filed: Aug. 5, 1975

[21] Appl. No.: 601,988

[30] Foreign Application Priority Data

Aug. 23, 1974 United Kingdom ............. 37232/74

[52] U.S. Cl. .............................. 424/326; 424/316; 424/322; 260/501.14; 260/552 R; 260/564 R; 260/564 E

[51] Int. Cl.$^2$ ....................................... C07C 123/00
[58] Field of Search .................. 260/564 R, 501.14; 424/326, 316

[56] References Cited
FOREIGN PATENTS OR APPLICATIONS 816,760   6/1974   Belgium .............................. 260/564

Primary Examiner—Gerald A. Schwartz
Attorney, Agent, or Firm—Connolly and Hutz

[57] ABSTRACT

The preparation of triazapentadienes with acaricidal and insecticidal properties is described.

16 Claims, No Drawings

TRIAZAPENTADIENES AS ACARICIDES AND INSECTICIDES

BACKGROUND OF THE INVENTION

All stages in the life cycle of ticks tend to damage the skins of afflicted animals and thereby spoil the state of the skins with the consequence that cattle hides and sheep skins intended for the manufacture of leather and sheep skin are reduced in quality. Furthermore, the ticks may facilitate the transmission of disease to the afflicted animal, and the general state of health and the quality of flesh of the animal may be detrimentally affected.

Belgian Pat. No. 816,760 describes a number of triazapentadienes as broad spectrum parasiticides. It is of importance to extend this series of compounds to include those that are useful for protecting plants from plant acarids such as phytophagous spider mites and plant insects such as pea aphids (hemiptera). Activity against the yellow fever mosquito (diptera) is very much desired.

SUMMARY OF THE INVENTION

This invention is concerned with the preparation of triazapentadienes of the formula:

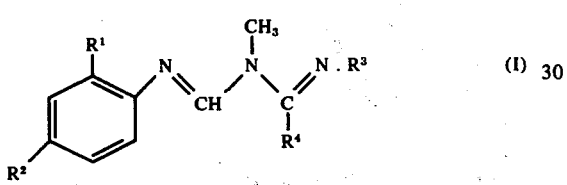

wherein
$R^1$ is alkyl of 1 to 4 carbon atoms;
$R^2$ is hydrogen, halogen or alkyl of 1 to 4 carbon atoms;
$R^3$ is cycloalkyl of 4 to 10 carbon atoms or cycloalkyl substituted by halogen or alkyl of 1 to 4 carbon atoms; alkyl of 1 to 4 carbon atoms substituted by phenyl or substituted phenyl; or alkyl of 1 to 4 carbon atoms substituted by cycloalkyl of 4 to 10 carbon atoms or cycloalkyl substituted by halogen or alkyl of 1 to 4 carbon atoms; and
$R^4$ is hydrogen, alkyl of 1 to 4 carbon atoms or a group $-SR^5$ where $R^5$ is hydrogen or alkyl of 1 to 4 carbon atoms; and the acid addition salts thereof.

DETAILED DESCRIPTION OF THE INVENTION

In this specification the term halogen means fluorine, chlorine, bromine, or iodine.

Alkyl groups containing three or more carbon atoms may be straight or branched chain. The preferred alkyl groups contain 1 or 2 carbon atoms.

Aryl as used herein includes substituted and unsubstituted aryl groups, e.g. phenyl groups optionally substituted by $C_1$–$C_4$ alkyl, $C_1$–$C_4$ alkoxy, halogen, trifluoromethyl, cyano, hydroxy, or an ester group of the formula $-COOR^6$ wherein $R^6$ is a $C_1$–$C_4$ alkyl group. The preferred aryl group is a phenyl group substituted by one or two $C_1$–$C_4$ alkyl or $C_1$–$C_4$ alkoxy groups.

Preferred cycloalkyl groups are unsubstituted and contain 5, 6 or 7, most preferably 5 or 6, carbon atoms in the ring.

$R^1$ is preferably a methyl group.
$R^2$ is preferably a methyl group or a chlorine atom.
$R^3$ is preferably an unsubstituted cyclopentyl or cyclohexyl group; a methyl or ethyl group substituted by a phenyl group, said phenyl group being optionally substituted by one or two $C_1$–$C_4$ alkyl or alkoxy groups; or a methyl or ethyl group substituted by an unsubstituted cyclopentyl or cyclohexyl group.

In one aspect $R^4$ is preferably a hydrogen atom. In another aspect $R^4$ is preferably a methyl or ethyl group, or a group of the formula $-SR^5$ wherein $R^5$ is a methyl or ethyl group.

Suitable acid addition salts include salts with weak dibasic organic acids, e.g. maleic, citraconic, tartaric or di-p-tolyl tartaric acid.

Particularly preferred individual compounds are the following:
1-cyclohexyl-5-(2,4-dimethylphenyl)-3-methyl-1,3,5-triazapenta-1,4-diene;
1-cyclopentyl-5-(2,4-dimethylphenyl)-3-methyl-1,3,5-triazapenta-1,4-diene;
1-cyclohexyl-5-(4-chloro-2-methylphenyl)-3-methyl-1,3,5-triazapenta-1,4-diene;
1-(2-{p-tolyl}ethyl)-5-(2,4-dimethylphenyl)-3-methyl-1,3,5-triazapenta-1,4-diene;
1-(2-{3,4-dimethoxyphenyl}ethyl)-5-(4-chloro-2-methyl phenyl)-3-methyl-1,3,5-triazapenta-1,4-diene;
1-(cyclohexylmethyl)-5-(4-chloro-2-methylphenyl)-3-methyl-1, 3,5-triazapenta-1,4-diene;
1-(cyclohexylmethyl)-5-(2,4-dimethylphenyl)-3-methyl-1,3,5-triazapenta-1,4-diene;
1-phenethyl-5-(4-chloro-2-methylphenyl)-3-methyl-1,3,5-triazapenta-1,4-diene;
1-(2-{3,4-dimethoxyphenyl}ethyl)-5-(2,4-dimethylphenyl)-3-methyl-1, 3,5-triazapenta-1,4-diene;
1-phenethyl-5-(2,4-dimethylphenyl)-3-methyl-1,3,5-triazapenta-1, 4-diene;
1-cyclohexyl-5-(2,4-dimethylphenyl)-2,3-dimethyl-1,3,5-triazapenta-1,4-diene;
1-cyclohexyl-5-(2,4-dimethylphenyl)-2-ethyl-3-methyl-1,3,5-triazapenta-1,4-diene; and
1-cyclopentyl-5-(2,4-dimethylphenyl)-2,3-dimethyl-1,3,5-triazapenta-1,4-diene.

It should be understood that compounds of the formula (I) in which $R^4$ is SH may exist predominantly in their tautomeric form, viz.,

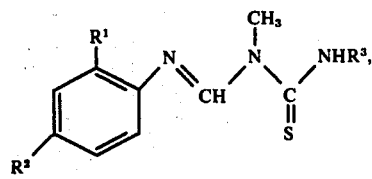

The compounds of the invention may be prepared via a number of routes, including the following:

1. Compounds in which $R^4$ is hydrogen may be prepared by reacting a formamidine of the formula:

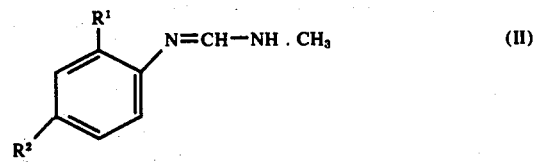

with an isonitrile of the formula $R^3.NC$. The reaction may be effected in the presence of a suitable catalyst, most preferably a cuprous catalyst such as cuprous oxide or cuprous chloride in a trace amount, a suitable reaction temperature being 50° to 80° C. Increase reaction temperatures are not generally recommended because they tend to increase the formation of by-products due to the reaction of one molecule of compound (II) with another such molecule. The reaction may be effected in the presence of a suitable inert organic solvent, such as benzene or toluene.

Generally, long reaction times of at least 48 hours are necessary.

Typically the product is recovered by evaporation of the reaction mixture in vacuo to leave an oil which may, if necessary, be purified by a conventional procedure such as treatment with neutral alumina in 40°–60° petroleum ether. The purified oil may crystallise on standing to give crystals of the desired product of the formula (I).

The isonitriles of the formula $R^3.NC$ and the formamidines of the formula (II) are either known compounds or may be prepared by procedures analogous to those of the prior art. Methods for the preparation of formamidines falling within the formula (II) are described for example in British Patent Specifications No. 964,640, 1,039,930 and 1,327,936.

2. a. Compounds in which $R^4$ is a hydrogen atom or a lower alkyl group may be prepared by reacting a formamidine of the formula:

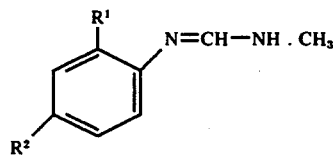

(II)

with an imidate of the formula:

(III)

wherein $R^7$ is a $C_1$–$C_4$ alkyl group and $R^4$ is as defined above in this method.

The reaction is typically carried out by heating the reactants together for several hours, followed by evaporating the resulting mixture to dryness, adding a suitable inert solvent such as iso-octane, filtering, purifying the filtrate by treatment with carbon and basic alumina, filtering again, adding further solvent, and finally cooling the filtrate to e.g. −60° C to crystallise the desired product out of solution. The product may, if desired, be purified by recrystallisation from a suitable solvent.

The imidates of the formula (III) are either known compounds or may be prepared by methods analogous to those of the prior art, e.g. as follows:

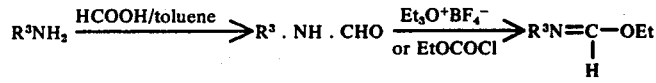

b. Conversely, it is also possible to prepare compounds in which $R^4$ is a hydrogen atom or a lower alkyl group by reacting an imidate of the formula:

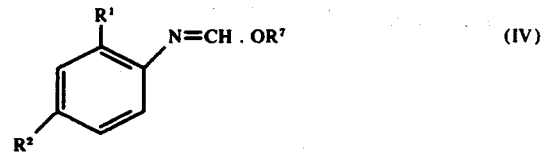

(IV)

wherein $R^7$ is a $C_1$–$C_4$ alkyl group, with an amidine of the formula:

(V)

3. Compounds of the formula (I) in which $R^4$ is a hydrogen atom or a $C_1$–$C_4$ alkyl group may be prepared by reacting an amidine of the formula:

(V)

with an isonitrile of the formula:

(VI)

The reaction and isolation of the product may be carried out in a similar manner to method (1) above, although in some cases it is possible to use reaction temperatures of above 80° C without substantially increasing the formation of by-products.

The starting materials of the formula (V) may be obtained in a conventional manner, e.g. by the reaction of an imidate of the formula:
with an amine of the formula $R^3NH_2$.

4. Compounds of the formula (I) in which $R^4$ is a group of the formula $-SR^5$ may be prepared by reacting a formamidine of the formula:

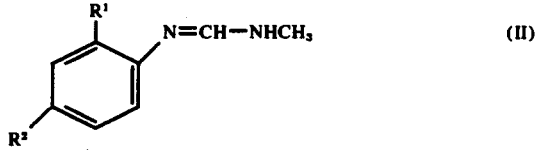

(II)

with an isothiocyanate of the formula $R^3.NCS$, thereby obtaining a product in which $R^5$ is a hydrogen atom, followed by, if desired, alkylating the said product with a suitable alkylating agent to obtain a compound in which $R^5$ is a $C_1$–$C_4$ alkyl group.

The reaction between the isothiocyanate and compound (II) may be carried out by stirring the reactants at room temperature in an inert solvent, e.g. ether, for up to 24 hours. The product may be obtained by removal of the solvent by evaporation, followed by trituration with e.g. 60°-80° petroleum ether. If desired, the product may be recrystallised from a suitable solvent, e.g. petroleum ether.

Alkylation may be carried out using a suitable alkylating agent, e.g. methyl fluorosulfonate ($F.SO_2.OCH_3$) or triethyloxonium fluoborate ($[Et]_3O^+BF_4^-$), in a conventional manner.

5. The salts of the compounds of the formula (I) may be made in a conventional manner, e.g. by mixing a solution of the free base in a suitable solvent, e.g. diethyl ether, with a solution of the acid in a suitable solvent, e.g. diethyl ether, and recovering the salt as a precipitate.

The compounds of the formula (I) have acaricidal activity, particularly against all stages in the life cycle, including gravid female ticks, of the cattle ticks *Boophilus microplus, Haemaphysalis longicornus, Rhipicephalus appendiculatus* and *Boophilus decoloratus*.

In one test, five freshly collected, fully engorged *Boophilus microplus* adult/female ticks are used for each acaricidal compound. Using a micro-pipette 10 micro-litres of a solution containing 10 micro-grams of the acaricidal compound in ethanol or acetone, is applied to the dorsal surface of each of the ticks. The treated ticks are placed in weighed 1 × 2 glass vials, weighed and stored at 26° C and 80% + R.H. in plastic boxes for two weeks. The ticks are then removed from the vials and the vials weighed to give the weight of eggs laid by the ticks. Any reduction in the egg laying of the treated ticks is calculated as a percentage of the eggs laid by untreated control ticks.

The eggs are returned to the incubator for a further 3 weeks after which time the percentage of eggs hatching is estimated.

The percentage reduction in the anticipated reproduction of the ticks is calculated using the weight of eggs laid and the percentage of eggs hatching.

The test may be repeated using smaller amounts of the acaricidal compound.

In another test, using a pipette 0.5 ml of a solution containing 0.5 mg of the acaricidal compound in ethanol or acetone is spread evenly on to a Whatman No. 1 filter paper 8 cm × 6.25 cm (50 sq. c.m.) to give a dosage of 100 mg/m².

The treated paper is allowed to dry at room temperature, folded with the treated surface inside and two short edges sealed with a crimping machine. The open ended envelope is placed in a 1 lb Kilner jar containing damp cotton wool in a plastic pot and stored in an incubator at 26° C for 24 hours. 20 – 50 *Boophilus microplus* larvae, which had latched 8 – 14 days previously, are placed in the envelope using a small spatula. The open end is then crimped to form a sealed packet. The treated paper containing the larvae is returned to the Kilner jar and kept for a further 48 hours in the incubator. 20 – 50 larvae are placed similarly in an untreated paper envelope to act as controls. At the end of the 48 hour test period the mortality is noted and recorded as a percentage after correction for any mortality among the untreated control ticks.

The test may be repeated using smaller amounts of the acaricidal compound.

In addition to percentage effectiveness figures, $ED_{50}$ results can be obtained from dose response measurements using any of the afore-described tests.

Activity against *Haemaphysalis longicornus* nymphs may be measured in a similar manner to the above larvae test.

The activity of the compounds of the Examples detailed hereinafter against the tick *Boophilus microplus* is set out in the following Table:

TABLE

| Example No. | *Boophilus Microplus* (in vitro) | | | | |
|---|---|---|---|---|---|
| | Larva (Contact) | | Adult (Topical) | | |
| | Dose (mg/m²) | % Kill | Dose (μg/tick) | % Reduct'n in egg laying | % Reduct'n in egg hatch |
| I and XVIX (free base) | 100 | 100 | 10 | 94 | 100 |
| | 12.5 | 100 | 4 | 81 | 97 |
| I (maleate salt) | 100 | 96 | 10 | 96 | 100 |
| I (citraconate salt) | 100 | 100 | 10 | 97 | 100 |
| II | 100 | 100 | 10 | 100 | 100 |
| III | 100 | 100 | 10 | 77 | 100 |
| | 12.5 | 100 | 4 | — | 87 |
| IV | 100 | 100 | 10 | 63 | 86 |
| | 12.5 | 96 | — | — | — |
| V | 100 | 100 | 10 | 90 | 100 |
| | 6.25 | 100 | 4 | — | 85 |
| VI | 100 | 100 | 10 | 57 | 87 |
| VII | 100 | 100 | 10 | 88 | 99 |
| | 6.25 | 100 | 8 | — | 83 |
| VIII | 100 | 100 | 10 | 79 | 100 |
| | 6.25 | 100 | 8 | — | 90 |
| IX | 100 | 100 | 10 | 99 | 100 |
| | 12.5 | 86 | 2 | — | 95 |
| X | 100 | 100 | 10 | 30 | 84 |
| | 12.5 | 100 | 8 | 61 | 99 |
| XI | 100 | 100 | 10 | 100 | 100 |

TABLE-continued

| Example No. | Larva (Contact) Dose (mg/m²) | % Kill | Adult (Topical) Dose (μg/tick) | % Reduct'n in egg laying | % Reduct'n in egg hatch |
|---|---|---|---|---|---|
| | 12.5 | 100 | 2 | 63 | 98 |
| XII | 100 | 100 | 10 | 99 | 100 |
| | — | — | 2 | 84 | 96 |
| XIII (free base) | 100 | 100 | 10 | 97 | 100 |
| | 1 | 100 | 8 | — | 95 |
| | 0.5 | 96 | 4 | — | 79 |
| XIII (citraconate salt) | 100 | 100 | 10 | 60 | 99 |
| | 12.5 | 91 | 8 | — | 85 |
| XIV | 100 | 100 | 10 | 90 | 99 |
| | 1 | 100 | 8 | — | 98 |
| | 0.5 | 98 | 4 | — | 87 |
| XV | 0.25 | 98 | 10 | — | 100 |
| XVI | 100 | 26 | 10 | 60 | 96 |
| | — | — | 8 | — | 90 |
| XVII | 100 | 100 | 10 | 32 | 70 |
| | 25 | 98 | — | — | — |
| XVIII | 100 | 100 | 10 | 14 | 23 |
| | 50 | 89 | — | — | — |

Thus the invention provides an acaricidal/or insecticidal composition comprising a compound of the formula (I) together with a diluent or carrier. The diluent or carrier may be a solid or a liquid, optionally together with a dispersing agent, emulsifying agent or wetting agent. The compositions of the invention include not only compositions in a suitable form for application but concentrated primary compositions which may be supplied to the user and which require dilution with a suitable quantity of water or other diluent prior to application. Typical compositions of the invention include, for example, dusting powders, dispersible powders, solutions, dispersions, emulsions and emulsifiable concentrates.

A dust may be made by mixing the appropriate amount of the finely divided active compound with a solid pulverlent diluent or carrier such as talc, clay, calcite, pyrophyllite, diatomaceous earth, walnut sheel flour, silica gel, hydrated alumina, or calcium silicate. As an alternative method of preparation, the diluent or carrier is mixed with a solution of the active compound in a volatile organic solvent such as benzene, the solvent being subsequently removed by evaporation. Preferably, the active compound will be present in the dust in an amount of from about 0.25 to about 4% by weight.

Dispersible powders, of special value for spray applications, may be made by adding a suitable dispersing agent to the active compound, or to a dust containing the active compound, so that a stable aqueous dispersion of the active compound is formed on mixing the powder with water. The dispersible powders preferably contain from about 25 to 75% by weight of the active compound.

Emulsifiable concentrates comprise a solution of the active compound in a substantially water-immiscible non-toxic organic solvent containing an emulsifying agent. Suitable solvents include, for example, toluene, xylene, petroleum oil, and alkylated naphthalenes. Preferably, the concentrate will contain 5–75 gms. of the active compound per 100 ml. of solution. The concentrates may be diluted with water prior to use to give a concentration of the active compound in the aqueous medium of from e.g. about 0.005 to about 0.1% w/v (g/100 ml.), or approximately 5 to 1000 p.p.m. The volatile solvents, e.g. toluene and xylene, evaporate after spraying to leave a deposit of the active ingredient. The made up spray or dip may be an emulsion or solution.

The compositions of the invention may be applied to ground, such as that around dairies, in order to combat e.g. cattle ticks thereon. However, it is preferred to treat animals by spraying them or passing them through animal dips.

Thus the present invention also provides a method for protecting animals, particularly cattle, from acarids, particularly cattle ticks, which comprises treating the animal externally with an acaricidal amount of a compound of the formula (I) or acaricidal composition as defined above.

The compositions of the invention may also contain a pesticide, fungicide, additional acaricide, or the like.

The invention is illustrated by the following Examples, in which all temperatures are given in °C. The compounds of the Examples were characterised by infra-red and nuclear magnetic resonance (n.m.r.) spectra, thin layer chromatography, and, in most cases, by melting point, analytical and mass spectral data. In the n.m.r. data, the protons responsible for the signals are underlined, $s$, $q$, $t$ and $m$ indicating, respectively, a singlet, quartet, triplet or multiplet.

EXAMPLE 1

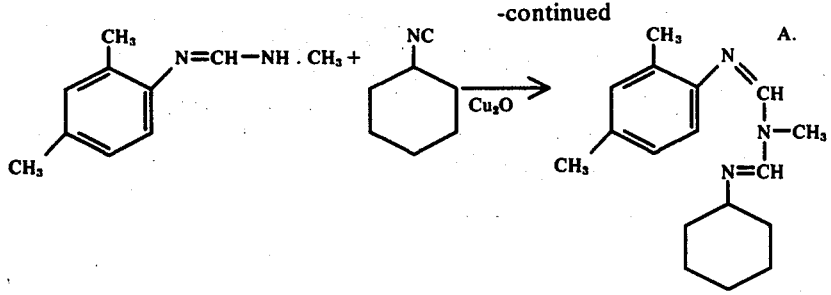

A mixture of N-2, 4-dimethylphenyl-N[1]-methyl formamidine (3.0 g, 0.0185M), cyclohexane isonitrile (2.01 g, 0.0185M), benzene (60 ml.) and cuprous oxide (trace amount) was refluxed for 2 hours. Evolution of methylamine was observed and heating was immediately stopped. The reaction was left at room temperature for nine days when analysis by thin layer chromatography (t.l.c.) indicated that a significant quantity of the amidine still remained in the reaction mixture. The mixture was then heated at about 70° for 8 hours, when t.l.c. analysis indicated that a small amount of the amidine still remained. After leaving overnight, the reaction mixture was heated at about 70° for a further six hours, filtered, and concentrated in vacuo to leave a deep red oil (4.7 g). The deep red oil was purified by treatment with neutral alumina in 40°–60° petroleum ether. Evaporation of the ether in vacuo afforded an almost colourless oil which crystallised on standing to yield large colourless prisms of 1-cyclohexyl-5-(2,4-dimethylphenyl)-3-methyl-1,3,5-triazapenta-1, 4-diene, m.p. 55°–57.5°.

Analysis: Found: C, 75.60; H, 9.40; N, 15.59%. Required: C, 75.24; H, 9.29; N, 15.48%. B. The monomaleate salt of the compound prepared in part A was prepared by dissolving the said compound (2.5 g) in diethyl ether (50 ml.), and adding the solution to a stirred solution of maleic acid (1.16 g) in diethyl ether (100 ml.). The resulting white precipitate, the monomaleate salt of 1-cyclohexyl5-(2,4-dimethylphenyl)-3-methyl-1,3,5-triazapenta-1,4-diene (2.6 g), had a melting point of 126.8° (decomp.) and was characterised by n.m.r. and i.r. spectra.

C. The mono-citraconate, tartrate and di-p-tolyltartrate salts of the compound prepared in part A above were also prepared by procedures similar to that described in part B. The salts were characterised by nuclear magnetic resonance and infra-red spectra, the melting point and analytical data for the citraconate salt being as follows: m.p. 128°–129°.

Analysis %: Found: C, 66.09; H, 7.82; N, 10.19; Calculated for $C_{17}H_{25}N_3.C_5H_6O_4$:C, 65.83; H, 7.73; N, 10.47.

In order to establish that these salts were ionic in/-character and not addition complexes, n.m.r. spectra of the free base and its salts were run in three solvents, with and without triethylamine being added. Chloroform was used as an internal standard for the/region under investigation.

The shifts of the indicated protons, A and B, are shown in the following Table.

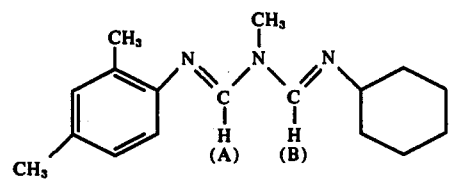

TABLE

| Sample | Free Base | | Citraconate Salt | | Tartrate Salt | | Di-p-tolyl Tartrate Salt | |
|---|---|---|---|---|---|---|---|---|
| Solvent | A (δ) | B (δ) | A (δ) | B (δ) | A (δ) | B (δ) | A (δ) | B (δ) |
| CDCl$_3$ | 7.83 | 7.92 | 8.40 | 9.17 | — | — | — | — |
| CDCl$_3$ + Et$_3$N | 7.75 | 7.85 | 7.72 | 7.80 | — | — | — | — |
| DMSOd$_6$ | 7.95 | 8.10 | 8.05 | 8.35 | 8.12 | 8.45 | 8.20 | 8.50 |
| DMSOd$_6$ + Et$_3$N | 7.90 | 8.05 | 7.92 | 8.02 | 7.91 | 8.03 | 7.92 | 8.01 |
| HMP | ←—6.67—→ | | 6.73 | 6.90 | 6.75 | 6.95 | 6.77 | 7.00 |
| HMP + Et$_3$N | ←—6.65—→ | | ←—6.63—→ | | ←—6.62—→ | | 6.64 | |

HMP = HEXAMETHYLPHOSPHORAMIDE.
DMSO = dimethylsulfoxide

No attempt was made to assign individual signals to protons A and B, but in each case the higher δ value was designated B, and the lower value A.

From the above it will be seen that there is a pronounced shift in the values for the indicated protons for the salt forms compared to the free base.

A shift to a higher δ-value occurs in complexing solvents such as DMSO and HMP. The large shifts observed are caused by the protonation of the adjacent nitrogen atoms. Although a shift in the value of protons A and B does occur in complexing or hydrogen bonding solvents, this shift increases further on salt formation, and may be reversed by the addition of triethylamine. This indicates that the salts are ionic in character and not simple addition complexes.

Full n.m.r. scans showed that in each case the salts were of a 1:1 ratio of base to the dibasic acid.

EXAMPLES II

The following compounds were prepared by procedures similar to that of Example I part A, using N-(2,4-dimethylphenyl)-N¹-methylformamidine or N-(4-chloro-2-methylphenyl)-N¹-methylformamidine, and the appropriate isonitrile, as starting materials:

was filtered through alumina, and concentrated to yield an oil (7.5 g) which partially solidified on standing to give an oily solid which with scratching on a porous plate gave the required compound, 1-cyclohexyl-2,3-dimethyl-5-(2, 4-dimethylphenyl)-1,3,5-triazapenta-1,4-diene, m.p. 37°–39°, molecular weight from mass spectra 285.

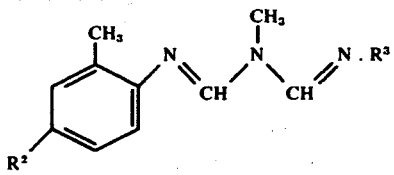

| Example No. | R² | R³ | M.P. °C | Analysis % (Theoretical in brackets) C | H | N | Molecular weights from mass spectral data |
|---|---|---|---|---|---|---|---|
| II | $CH_3-$ | cyclopentyl | oil | 74.70 (74.67 | 9.10 9.01 | 16.25 16.33) | 257 |
| III | $Cl-$ | cyclohexyl | 79–80° | 65.79 (65.85 | 7.60 7.60 | 14.27 14.39) | — |
| IV | $Cl-$ | cyclopentyl | oil | 64.30 (64.85 | 7.44 7.26 | 13.44 15.12) | 277 |
| V | $CH_3-$ | $CH_3-\langle\underline{\phantom{O}}\rangle-CH_2CH_2-$ | oil | 78.26 (78.13 | 8.29 8.20 | 12.41 13.67) | 307 |
| VI | $Cl-$ | $CH_3-\langle\underline{\phantom{O}}\rangle-CH_2CH_2-$ | oil | 69.28 (69.60 | 6.68 6.76 | 12.81 12.82) | 327 |
| VII | $Cl-$ | $CH_3O-\langle\underline{\phantom{O}}\rangle-CH_2CH_2-$ (CH₃O) | oil | 64.43 (64.25 | 6.63 6.47 | 11.73 11.24) | 373 |
| VIII | $Cl-$ | $\langle\underline{\phantom{O}}\rangle-CH_2-$ | oil | 67.01 (66.76 | 8.09 7.91 | 13.77 13.74) | 305 |
| IX | $CH_3-$ | $\langle\underline{\phantom{O}}\rangle-CH_2-$ | oil | 75.74 (75.74 | 9.62 9.53 | 14.39 14.72) | 285 |
| X | $Cl-$ | $\langle\underline{\phantom{O}}\rangle-CH_2CH_2-$ | oil | 68.37 (68.89 | 6.48 6.42 | 13.19 13.39) | 313 |
| XI | $CH_3-$ | $CH_3O-\langle\underline{\phantom{O}}\rangle-CH_2CH_2-$ (CH₃O) | oil | 71.17 (71.36 | 7.83 7.70 | 11.84 11.89) | 353 |
| XII | $CH_3-$ | $\langle\underline{\phantom{O}}\rangle-CH_2CH_2-$ | oil | 78.10 (77.78 | 8.04 7.90 | 13.26 14.32) | 293 |

EXAMPLE III

A. To a solution of methyl N-methylacetimidate (8.7 g, 0.1m) in toluene (90 ml.) was added cyclohexylamine (10.5 g, 0.105m). After 72 hours at room temperature and 32 hours heating at 60°–70° C the solvent was removed by evaporation to yield an oil which crystallised on cooling. Chromatography on alumina using ether as eluent afforded N-cyclohexyl-N¹-methylacetamidine as a colourless solid (11 g), or m.p. 108.5° – 109.5° C.

Analysis: Found: C, 70.22; H, 11.92; N, 17.92%. $C_9H_{18}N_2$ requires: C, 70.08; H, 11.76; N, 18.15%.

B. A solution of N-cyclohexyl-N¹-methylacetamidine (prepared in part A above) (4.11g, 0.027m) and 2,4-dimethylphenyl isocyamide (3.88 g, 0.03m) in dry toluene (30 ml) in the presence of a trace amount of $Cu_2O$ was kept at room temperature for 150 hours, heated at 80°–85° for 14 hours and refluxed for 2½ hours, during which time the course of the reaction was monitored by n.m.r. spectroscopy. The resulting deep red solution Analysis: Found: C, 75.77; H, 9.60; N, 15.00%. Required for $C_{18}H_{27}N_3$: C, 75.75; H, 9.54; N, 14.72%.

C. The citraconate salt of the triazapenta-1,4-diene product of part B was prepared by adding a solution of the citraconic acid (260 mg., 0.002m) in dry ether (10 ml) dropwise at room temperature to a solution of the said triazapenta-1,4-diene (570 mg, 0.002m) in dry ether (10 ml.). The resulting precipitate, the monocitraconate of 1-cyclohexyl-2, 3-dimethyl-5-(2,4-dimethylphenyl)-1,3,5-triazapenta-1,4-diene (770 mg.), m.p. 101°–103°, was filtered off and crystallised from ethyl acetate/40°–60° petroleum ether.

Analysis: Found: C, 66.34; H, 8.12; N, 9.97%. Required for $C_{23}H_{33}N_3O_4$: C, 66.48; H, 8.01; N, 10.11%.

If desired, the triazapenta-1,4-diene free base may be liberated from the citraconate salt by treatment with e.g. triethylamine in ether.

EXAMPLES IV

The following compounds were prepared by the method of Example III part B, starting from the appropriate amidine and 2,4-dimethylphenylisocyanide:

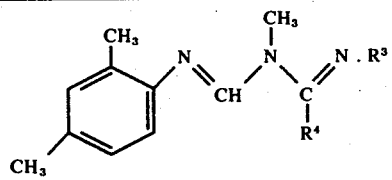

| Example No. | R³ | R⁴ | M.P. (°C) | Analysis % or n.m.r./i.e. (Theoretical in brackets) C | H | N | Molecular weights from mass spectral data |
|---|---|---|---|---|---|---|---|
| XIV | cyclopentyl | CH₃— | 71–73° | 75.01 (75.24 | 9.18 9.29 | 15.00 15.48) | 271 |
| XV | cyclohexyl | CH₃CH₂— | oil | n.m.r. (CDCl₃): N—CH₃ τ6.65 (s,3H); —CH₂CH₃ τ7.5 (q,2H); —CH₂CH₃ τ8.9 (t,3H); 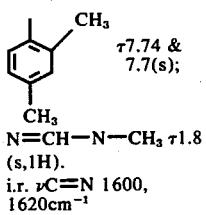 τ7.74 & 7.7(s); N=CH—N—CH₃ τ1.8 (s,1H). i.r. νC=N 1600, 1620 cm⁻¹ | | | 299 |

EXAMPLE V

A mixture of N-(2,4-dimethylphenyl)-N'-methylformamidine (8.1 g, 0.05 mole) and cyclohexylisothiocyanate (7.1 g, 0.05 mole) in dry ether (60 ml.) was stirred at room temperature (25° C) for 18 hours. Removal of the solvent by evaporation, followed by trituration with petroleum ether, furnished a solid, N'-(cyclohexylthiocarbamoyl)-N-(2,4-di-methylphenyl)-N'-methylformamidine, which was recrystallised from petroleum ether (b.p. 60°–80°) to give the pure product, (6.2 g), m.p. 88°. An alternative name for the product is 1-cyclohexyl-5-(2,4-dimethyl)/phenyl-3-methyl-1,3,5-triazapent-4-en-2-thione.

Analysis: Found: C, 67.49; H, 8.31; N, 13.97%
C₁₇H₂₅N₃S requires: C, 67.33; H, 8.25; N, 13.86%

EXAMPLE VI

A solution of the thiocarbamoyl formamidine prepared in Example V above (3.03 g, 0.01 mole) in dry methylene chloride (30 ml.) was treated with methylfluorosulphonate (1 ml, 0.01 mole) and the solution was left at room temperature for 24 hours. The resulting mixture was treated with a slight excess of triethylamine and diluted with petroleum ether (b.p. 60°–80°) (100 ml.), when two layers separated. The upper layer was separated off and the solvent removed in vacuo to give, as a colourless viscous oil, 1-cyclohexyl-5-(2,4-dimethylphenyl)-3-methyl-2-methylthio-1,3,5-triazapenta-1,4-diene (2.45 g), molecular weight from mass spectral data 317.

n.m.r. (CDCl₃): N=CH—N τ1.58(s,1H); —N—CH₃ τ6.6(s,3H);

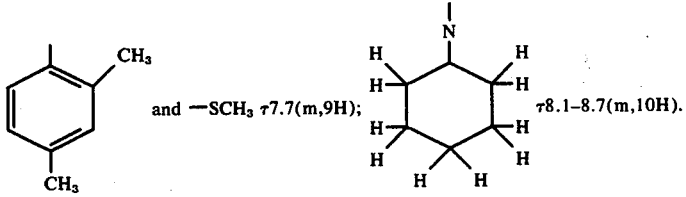

i.r. νC=N 1640, 1600 cm⁻¹.

EXAMPLE VII

A mixture of N'-(cyclohexylthiocarbamoyl)-N-(2,4-dimethylphenyl)-N'-methylformamidine (1.0 g) and triethyloxoniumfluoborate (1.3 g) in methylene chloride (15 ml.) was left overnight at room temperature. The solution was then heated with excess triethylamine and diluted with diethyl ether to precipitate triethyl ammonium fluoborate which was filtered off. The filtrate on evaporation furnished a yellow oil which would not solidify on trituration with ether and other solvents. The filtrate was chromatographed on a short column of silica and eluted with ethyl acetate, the desired product, 1-cyclohexyl-5-(2,4-dimethylphenyl)-3-methyl-2-ethylthio-1, 3,5-triazapenta-1,4-diene, being in the 2nd fraction (each fraction 35 ml.); molecular weight from mass spectral data 331.

n.m.r. (CDCl₃): N—CH₃ τ6.6 (s,3H); N=CH—N τ1.55 (s,1H); S—CH₂—CH₃

τ7.25 (q,2H); 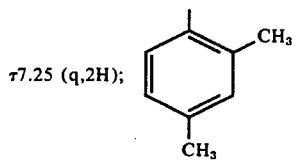 τ7.71–7.69(broad s,3H); —SCH₂—CH₃ τ8.72 (t,3H).

i.r. νC=N 1640, 1600 cm⁻¹.

EXAMPLE VIII

A. Formic acid (90%, 4.02 l) was added to a solution of cyclohexylamine (3 kg.) in toluene (10 l) over 2 hours during which time the temperature increased to 92° C. The resulting two-phase mixture was refluxed under Dean-Stark conditions for 18 hours by which time water evolution had ceased. The solvent was removed by evaporation in vacuo and the product, N-cyclohexylformamide (3.837 kg.), distilled directly b.p.≈165°/18mmHg.

B. To a suspension of triethyloxonium fluoroborate (1326 g.) in ether (4 l) was added N-cyclohexylformamide (806 g) over 1½ hours under a blanket of nitrogen. After stirring for 5 hours and standing overnight the layers were separated and the lower layer washed with ether (2 × 2l). Further ether (3 l) was added followed by triethylamine until basic. After stirring for a further 30 minutes the solid was collected and washed with ether. The combined filtrate and washings were evaporated and the product, ethyl N-cyclohexylformimidate, (615 g) distilled. b.p. 85°–87°C/40 mm Hg.

C. A solution of 2,4-xylidine (3 kg.) in ether (12 l) was treated with a slow stream of hydrogen chloride until salt formation was complete. The product, 2,4-xylidine hydrochloride (3.7 kg.) was collected, washed with ether and dried in vacuo. To a slurry of 2,4-xylidine hydrochloride (32 g) and N-methylformamide (35.4 g) in dry toluene (160 ml) was added benzenesulphonyl chloride (40.6 g) over 15 minutes. After stirring at ambient temperature overnight water (406 ml.) was added, the layers separated and the aqueous layer basified to pH9 with 50% aqueous caustic soda solution. The solid formed, N-methyl-N¹-(2,4-dimethylphenyl)-formamidine, (31 g) was filtered, washed copiously with water and dried in vacuo at 50° C.

D. A mixture of N- methyl -N'-(2,4-dimethylphenyl)-formamidine (20 g) and ethyl N-cyclohexylformimidate (40 g) was stirred and heated at 70°–75° C under a pressure of 20 mm/Hg for 1½ hours. The mixture was then evaporated, iso-octane (400 ml.) added to the residue, and, after stirring for 1 hour, some insoluble material removed. The filtrate was treated with carbon ("Norit", 5g) and basic alumina (5 g), diluted with further iso-octane (50 ml.) and cooled to −60° C. The white crystalline solid was rapidly filtered, washed with iso-octane (50 ml. at −60° C) and petroleum ether (b.p. 30°–40° C − 50 ml. at −60° C) and dried in vacuo at 35° C. The product (30 g) was found by analysis and melting point data to be identical to the product of Example 1, viz. 1-cyclohexyl-5-(2,4-dimethylphenyl)-3-methyl-1,3,5-triazapenta-1,4-diene.

A suitable composition for an emulsifiable concentrate containing a compound of the invention may be as follows:

EXAMPLE IX

The constituents of an emulsifiable concentrate are as follows:

| | |
|---|---|
| 1-cyclohexyl-5-(2,4-dimethylphenyl)-3-methyl-1,3,5-triazapenta-1,4-diene (product of Example I) | 5–75 % w/v |
| Emulsifiers(s) | up to 20 % w/v |
| "Aromasol H" (mixed hydrocarbon solvent) | balance to 100 % |

The concentrate may be prepared by mixing the emulsifier(s) and solvent until homogeneous, adding the compound prepared in Example I, and stirring until dissolution occurs.

What is claimed is:

1. A compound of the formula:

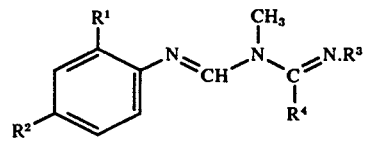

wherein

R¹ is alkyl of 1 to 4 carbon atoms;
R² is hydrogen, halogen or alkyl of 1 to 4 carbon atoms;
R³ is cycloalkyl of 4 to 10 carbon atoms, or cycloalkyl substituted by halogen or alkyl of 1 to 4 carbon atoms; alkyl of 1 to 4 carbon atoms substituted by phenyl or phenyl substituted by one or two $C_1$–$C_4$ alkyl or $C_1$–$C_4$ alkoxy groups; or alkyl of 1 to 4 carbon atoms substituted by cycloalkyl of 4 to 10 carbon atoms or cycloalkyl substituted by halogen or alkyl of 1 to 4 carbon atoms; and
R⁴ is hydrogen or alkyl of 1 to 4 carbon atoms; and the pesticidally acceptable acid addition salts thereof.

2. 1-Cyclohexyl-5-(2,4-dimethylphenyl)-1,3,5-triazapenta-1,4-diene.

3. 1-Cyclopentyl-5-(2,4-dimethylphenyl)-3-methyl-1,3,5-triazapenta-1,4-diene.

4. 1-Cyclohexyl-5-(4-chloro-2-methylphenyl)-3-methyl-1,3,5-triazapenta-1,4-diene.

5. 1-(2-[p-Tolyl]ethyl)-5-(2,4-dimethylphenyl)-3-methyl-1,3,5-triazapenta-1,4-diene.

6. 1-(2-[3,4-Dimethoxyphenyl]ethyl)-5-(4-chloro-2-methylphenyl)-3-methyl-1,3,5-triazapenta-1,4-diene.

7. 1-(Cyclohexylmethyl)-5-(4-chloro-2-methylphenyl)-3-methyl-1,3,5-triazapenta-1,4-diene.

8. 1-(Cyclohexylmethyl)-5-(2,4-dimethylphenyl)-3-methyl-1,3,5-triazapenta-1,4-diene.

9. 1-Phenethyl-5-(4-chloro-2-methylphenyl)-3-methyl-1,3,5-triazapenta-1,4-diene.

10. 1-(2-[3,4-Dimethoxyphenyl]ethyl)-5-(2,4-dimethylphenyl)-3-methyl-1,3,5-triazapenta-1,4-diene.

11. 1-Phenethyl-5-(2,4-dimethylphenyl)-3-methyl-1,3,5-triazapenta-1,4-diene.

12. 1-Cyclohexyl-5-(2,4-dimethylphenyl)-2,3-dimethyl-1,3,5-triazapenta-1,4-diene.

13. 1-Cyclohexyl-5-(2,4-dimethylphenyl)-2-ethyl-3-methyl-1,3,5-triazapenta-1,4-diene.

14. 1-Cyclopentyl-5-(2,4-dimethylphenyl)-2,3-dimethyl-1,3,5-triazapenta-1,4-diene.

15. An acaricidal or insecticidal composition comprising an effective amount of a compound of claim 1 and a diluent or carrier.

16. A method of combatting ectoparasites on animals which comprises contacting said animals with an effective amount of a compound of claim 1.

* * * * *